US006676939B2

(12) United States Patent
Hurst et al.

(10) Patent No.: US 6,676,939 B2
(45) Date of Patent: Jan. 13, 2004

(54) METHODS OF MODULATING IL-174 RESPONSE

(75) Inventors: Stephen D. Hurst, Palo Alto, CA (US); Sandra M. Zurawski, San Juan Bautista, CA (US); Donna M. Rennick, Los Altos, CA (US)

(73) Assignee: Schering Corporation, Kenilworth, NJ (US)

( * ) Notice: Subject to any disclaimer, the term of this patent is extended or adjusted under 35 U.S.C. 154(b) by 35 days.

(21) Appl. No.: 09/836,385

(22) Filed: Apr. 17, 2001

(65) Prior Publication Data

US 2003/0165460 A1 Sep. 4, 2003

Related U.S. Application Data

(60) Provisional application No. 60/198,488, filed on Apr. 18, 2000.

(51) Int. Cl.[7] .............................................. A61K 39/395
(52) U.S. Cl. ................ 424/139.1; 424/130.1; 424/133.1; 424/141.1; 530/351; 514/2
(58) Field of Search ........................ 424/134.1, 139.1; 530/351

(56) References Cited

U.S. PATENT DOCUMENTS

| 6,562,578 | B1 | * | 5/2003 | Gorman et al. |
| 2003/0008815 | A1 | * | 1/2003 | Chen et al. |

FOREIGN PATENT DOCUMENTS

| WO | WO 00/42188 | 7/2000 |

OTHER PUBLICATIONS

Rhan et al. Transgenic overexpression of human IL–17[E] results in eosinophilia, B–lyphocyte hyperplasia, and altered antibody production. 2002. Blood, 100(7): 2330–2340.*
Pan et al., Forced expression of murine IL–17E induces growth retardation, jaundice, a Th2–based response, and multiorgan inflammation in mice. 2001. J. Immunol., 167(11): 6559–67.*
Ashok R. Amin, PhD, and Steven B. Abramson, MD, *Curr. Op. Rheumatol.*, 10:263–268, 1998. "The role of nitric oxide in articular cartilage breakdown in osteoarthritis".
Martine Chabaud, et el. *J of Immunol.*, 161: 409–414, 1998. "Enhancing Effect of IL–17 on IL–1 Induced IL–6 and Leukemia Inhibitory Factor Production by Rheumatoid Arthritis Synoviocytes and Its Regulations by Th2 Cytokines[1]".

François Fossiez, et al., *Int. Rev. Immunol.*, 16(5–6):541–551, 1998, "Interleukin–17".
Mary Hitt, et al., *Advances in Pharmacology*, 40:137–206, 1997. Human Adenovirus Vectors for Gene Transfer into Mammalian Cells.
Neil W. Isaacs, *Curr. Op. Struct. Biol.*, 5:391–395, 1995 "Cystine knots".
Jacqueline Kennedy, et al., *J. Interferon and Cytokine Research*, 16:611–617, 1996. "Mouse IL–17: A Cytokine Preferentially Expressed by αβTCR+CD4–CD8– T Cells".
Andrea Knappe, et al., *J. Virology*, 72(7):5797–5801, Jul. 1998. "The Interleukin–17 Gene of Herpesvirus Saimiri".
Neil Q. McDonald and Wayne A. Hendrickson, *Cell*, 73:421–424, May 7, 1993. "A Structural Superfamily of Growth Factors Containing a Cystine Knot Motif".
Eric Rouvier, et al., *J. Immunol.*, 150(12):5445–5456, Jun. 15, 1993. "CTLA–8, Cloned from an Activated T Cell, Bearing AU–Rich Messenger RNA Instability Sequences, and Homologous to a Herpesvirus Saimiri Gene[1]".
Heng–Fong Seow, *Vet. Immunol. Immunopath.*, 63:139–148, 1998. "Pathogen interactions with cytokines and host defence: an overview".
Tali Shalom–Barak, et al., *J. Biological Chem.*, 273 (42): 27467–27473, Oct. 16, 1998. "Interleukin–17–induced Gene Expression in Articular Chondrocytes Is Associated with Activation of Mitogen–activated Protein Kinases and NF–kB".
Peter D. Sun and David R. Davies, *Annu. Rev. Biophys. Biomol. Struct.*, 24:269–291, 1995. "The Cystine–Knot Growth–Factor Superfamily".
Marcel Teunnison, et. al., *J. Ivest. Dermatol.*, 111:645–649, 1998. "Interleukin–17 and Interferon–γ Synergize in the Enhancement of Proinflammatory Cytokine Production by Human Keratinocytes".
Cees Van Kooten, et al., *J. Am. Soc. Nephrol.*, 9:1526–1534, 1998. "Interleukin–17 Activates Human Renal Epithelial Cells in Vitro and Is Expressed during Renal Allograft Rejection".
Zhengbin Yao, et al., *Immunity*, 3:811–821, Dec. 1995. "Herpesvirus Saimiri Encodes a New Cytokine, IL–17, Which Binds to a Novel Cytokine Receptor".
Zhengbin Yao, et al., *J. Immunol.*, 155:5483–5486, 1995. "Human Il–17: A Novel Cytokine Derived from T Cells".

* cited by examiner

*Primary Examiner*—Lorraine Spector
*Assistant Examiner*—Dong Jiang
(74) *Attorney, Agent, or Firm*—Edwin P. Ching; Tom Brody

(57) ABSTRACT

Agonists or antagonists of cytokine designated IL-174, and various methods of their use are provided. In particular, the methods make use of facts that many activities of the IL-174 cytokine are described.

5 Claims, No Drawings

SEQUENCE LISTING

```
<160> NUMBER OF SEQ ID NOS: 4

<210> SEQ ID NO 1
<211> LENGTH: 504
<212> TYPE: DNA
<213> ORGANISM: primate
<220> FEATURE:
<221> NAME/KEY: CDS
<222> LOCATION: (19)..(501)
<221> NAME/KEY: mat_peptide
<222> LOCATION: (67)..(501)

<400> SEQUENCE: 1
tgagtgtgca gtgccagc atg tac cag gtg gtt gca ttc ttg gca atg gtc        51
                    Met Tyr Gln Val Val Ala Phe Leu Ala Met Val
                        -15                     -10 atg gga acc cac acc tac agc cac tgg ccc agc tgc tgc ccc agc aaa        99
Met Gly Thr His Thr Tyr Ser His Trp Pro Ser Cys Cys Pro Ser Lys
 -5              -1   1               5                      10 ggg cag gac acc tct gag gag ctg ctg agg tgg agc act gtg cct gtg       147
Gly Gln Asp Thr Ser Glu Glu Leu Leu Arg Trp Ser Thr Val Pro Val
                15                  20                  25 cct ccc cta gag cct gct agg ccc aac cgc cac cca gag tcc tgt agg       195
Pro Pro Leu Glu Pro Ala Arg Pro Asn Arg His Pro Glu Ser Cys Arg
            30                  35                  40 gcc agt gaa gat gga ccc ctc aac agc agg gcc atc tcc ccc tgg aga       243
Ala Ser Glu Asp Gly Pro Leu Asn Ser Arg Ala Ile Ser Pro Trp Arg
        45                  50                  55 tat gag ttg gac aga gac ttg aac cgg ctc ccc cag gac ctg tac cac       291
Tyr Glu Leu Asp Arg Asp Leu Asn Arg Leu Pro Gln Asp Leu Tyr His
```

```
gcc cgt tgc ctg tgc ccg cac tgc gtc agc cta cag aca ggc tcc cac    339
Ala Arg Cys Leu Cys Pro His Cys Val Ser Leu Gln Thr Gly Ser His
             80                  85                  90 atg gac ccc cgg ggc aac tcg gag ctc ctc tac cac aac cag act gtc    387
Met Asp Pro Arg Gly Asn Ser Glu Leu Leu Tyr His Asn Gln Thr Val
         95                 100                 105 ttc tac cgg cgg cca tgc cat ggc gag aag ggc acc cac aag ggc tac    435
Phe Tyr Arg Arg Pro Cys His Gly Glu Lys Gly Thr His Lys Gly Tyr
            110                 115                 120 tgc ctg gag cgc agg ctg tac cgt gtt tcc tta gct tgt gtg tgt gtg    483
Cys Leu Glu Arg Arg Leu Tyr Arg Val Ser Leu Ala Cys Val Cys Val
        125                 130                 135 cgg ccc cgt gtg atg ggc tag                                        504
Arg Pro Arg Val Met Gly
140                 145

<210> SEQ ID NO 2
<211> LENGTH: 161
<212> TYPE: PRT
<213> ORGANISM: primate

<400> SEQUENCE: 2

Met Tyr Gln Val Val Ala Phe Leu Ala Met Val Met Gly Thr His Thr
    -15                 -10                  -5                  -1

Tyr Ser His Trp Pro Ser Cys Cys Pro Ser Lys Gly Gln Asp Thr Ser
 1               5                  10                  15

Glu Glu Leu Leu Arg Trp Ser Thr Val Pro Val Pro Pro Leu Glu Pro
             20                  25                  30

Ala Arg Pro Asn Arg His Pro Glu Ser Cys Arg Ala Ser Glu Asp Gly
         35                  40                  45

Pro Leu Asn Ser Arg Ala Ile Ser Pro Trp Arg Tyr Glu Leu Asp Arg
     50                  55                  60

Asp Leu Asn Arg Leu Pro Gln Asp Leu Tyr His Ala Arg Cys Leu Cys
 65                  70                  75                  80

Pro His Cys Val Ser Leu Gln Thr Gly Ser His Met Asp Pro Arg Gly
             85                  90                  95

Asn Ser Glu Leu Leu Tyr His Asn Gln Thr Val Phe Tyr Arg Arg Pro
            100                 105                 110

Cys His Gly Glu Lys Gly Thr His Lys Gly Tyr Cys Leu Glu Arg Arg
        115                 120                 125

Leu Tyr Arg Val Ser Leu Ala Cys Val Cys Val Arg Pro Arg Val Met
    130                 135                 140

Gly
145

<210> SEQ ID NO 3
<211> LENGTH: 985
<212> TYPE: DNA
<213> ORGANISM: rodent
<220> FEATURE:
<221> NAME/KEY: CDS
<222> LOCATION: (1)..(507)
<221> NAME/KEY: mat_peptide
<222> LOCATION: (49)..(507)

<400> SEQUENCE: 3 atg tac cag gct gtt gca ttc ttg gca atg atc gtg gga acc cac acc     48
Met Tyr Gln Ala Val Ala Phe Leu Ala Met Ile Val Gly Thr His Thr
    -15                 -10                  -5                  -1
```

```
gtc agc ttg cgg atc cag gag ggc tgc agt cac ttg ccc agc tgc tgc      96
Val Ser Leu Arg Ile Gln Glu Gly Cys Ser His Leu Pro Ser Cys Cys
 1               5                  10                  15 ccc agc aaa gag caa gaa ccc ccg gag gag tgg ctg aag tgg agc tct     144
Pro Ser Lys Glu Gln Glu Pro Pro Glu Glu Trp Leu Lys Trp Ser Ser
             20                  25                  30 gca tct gtg tcc ccc cca gag cct ctg agc cac acc cac cac gca gaa     192
Ala Ser Val Ser Pro Pro Glu Pro Leu Ser His Thr His His Ala Glu
         35                  40                  45 tcc tgc agg gcc agc aag gat ggc ccc ctc aac agc agg gcc atc tct     240
Ser Cys Arg Ala Ser Lys Asp Gly Pro Leu Asn Ser Arg Ala Ile Ser
     50                  55                  60 cct tgg agc tat gag ttg gac agg gac ttg aat cgg gtc ccc cag gac     288
Pro Trp Ser Tyr Glu Leu Asp Arg Asp Leu Asn Arg Val Pro Gln Asp
 65                  70                  75                  80 ctg tac cac gct cga tgc ctg tgc cca cac tgc gtc agc cta cag aca     336
Leu Tyr His Ala Arg Cys Leu Cys Pro His Cys Val Ser Leu Gln Thr
                 85                  90                  95 ggc tcc cac atg gac ccg ctg ggc aac tcc gtc cca ctt tac cac aac     384
Gly Ser His Met Asp Pro Leu Gly Asn Ser Val Pro Leu Tyr His Asn
            100                 105                 110 cag acg gtc ttc tac cgg cgg cca tgc cat ggt gag gaa ggt acc cat     432
Gln Thr Val Phe Tyr Arg Arg Pro Cys His Gly Glu Glu Gly Thr His
        115                 120                 125 cgc cgc tac tgc ttg gag cgc agg ctc tac cga gtc tcc ttg gct tgt     480
Arg Arg Tyr Cys Leu Glu Arg Arg Leu Tyr Arg Val Ser Leu Ala Cys
130                 135                 140 gtg tgt gtg cgg ccc cgg gtc atg gct tagtcatgct caccacctgc           527
Val Cys Val Arg Pro Arg Val Met Ala
145                 150 ctgaggctga tgcccggttg ggagagaggg ccaggtgtac aatcaccttg ccaatgcggg   587
ccgggttcaa gccctccaaa gccctacctg aagcagcagg ctcccgggac aagatggagg   647
acttggggag aaactctgac ttttgcactt ttttggaagca cttttgggaa ggagcaggtt  707
ccgcttgtgc tgctagagga tgctgttgtg gcatttctac tcaggaacgg actccaaagg   767
cctgctgacc ctggaagcca tactcctggc tcctttcccc tgaatccccc aactcctggc   827
acaggcactt tctccacctc tcccccttg ccttttgttg tgtttgtttg tgcatgccaa    887
ctctgcgtgc agccaggtgt aattgccttg aaggatggtt ctgaggtgaa agctgttatc   947
gaaagtgaag agatttatcc aaataaacat ctgtgttt                           985

<210> SEQ ID NO 4
<211> LENGTH: 169
<212> TYPE: PRT
<213> ORGANISM: rodent

<400> SEQUENCE: 4

Met Tyr Gln Ala Val Ala Phe Leu Ala Met Ile Val Gly Thr His Thr
    -15                 -10                 -5                  -1

Val Ser Leu Arg Ile Gln Glu Gly Cys Ser His Leu Pro Ser Cys Cys
 1               5                  10                  15

Pro Ser Lys Glu Gln Glu Pro Pro Glu Glu Trp Leu Lys Trp Ser Ser
             20                  25                  30

Ala Ser Val Ser Pro Pro Glu Pro Leu Ser His Thr His His Ala Glu
         35                  40                  45

Ser Cys Arg Ala Ser Lys Asp Gly Pro Leu Asn Ser Arg Ala Ile Ser
     50                  55                  60
```

-continued

```
Pro Trp Ser Tyr Glu Leu Asp Arg Asp Leu Asn Arg Val Pro Gln Asp
 65                  70                  75                  80

Leu Tyr His Ala Arg Cys Leu Cys Pro His Cys Val Ser Leu Gln Thr
                 85                  90                  95

Gly Ser His Met Asp Pro Leu Gly Asn Ser Val Pro Leu Tyr His Asn
                100                 105                 110

Gln Thr Val Phe Tyr Arg Arg Pro Cys His Gly Glu Glu Gly Thr His
            115                 120                 125

Arg Arg Tyr Cys Leu Glu Arg Arg Leu Tyr Arg Val Ser Leu Ala Cys
        130                 135                 140

Val Cys Val Arg Pro Arg Val Met Ala
145                 150
```

METHODS OF MODULATING IL-174 RESPONSE

This application claims benefit of U.S. provisional patent application No. 60/198,488, filed Apr. 18, 2000.

FIELD OF THE INVENTION

The present invention relates to compositions related to proteins which function in controlling physiology, development, and differentiation of mammalian cells, e.g., cells of a mammalian immune system. In particular, it provides nucleic acids, proteins, antibodies, and mimetics which regulate cellular physiology, development, differentiation, or function of various cell types, including hematopoietic cells.

BACKGROUND OF THE INVENTION

The immune system of vertebrates consists of a number of organs and several different cell types. Two major cell types include the myeloid and lymphoid lineages. Among the lymphoid cell lineage are B cells, which were originally characterized as differentiating in fetal liver or adult bone marrow, and T cells, which were originally characterized as differentiating in the thymus. See, e.g., Paul (ed. 1998) *Fundamental Immunology* (4th ed.) Raven Press, New York.

In many aspects of the development of an immune response or cellular differentiation, soluble proteins known as cytokines play a critical role in regulating cellular interactions. These cytokines apparently mediate cellular activities in many ways. They have been shown, in many cases, to modulate proliferation, growth, and differentiation of hematopoietic stem cells into the vast number of progenitors composing the lineages responsible for an immune response.

However, the cellular molecules which are expressed by different developmental stages of cells in these maturation pathways are still incompletely identified. Moreover, the roles and mechanisms of action of signaling molecules which induce, sustain, or modulate the various physiological, developmental, or proliferative states of these cells is poorly understood. Clearly, the immune system and its response to various stresses had relevance to medicine, e.g., infectious diseases, cancer related responses and treatment, allergic and transplantation rejection responses. See, e.g., Thorn, et al. *Harrison's Principles of Internal Medicine* McGraw/Hill, N.Y.

Medical science relies, in large degree, on appropriate recruitment or suppression of the immune system in effecting cures for insufficient or improper physiological responses to environmental factors. However, the lack of understanding of how the immune system is regulated or differentiates has blocked the ability to advantageously modulate the normal defensive mechanisms to biological challenges. Medical conditions characterized by abnormal or inappropriate regulation of the development or physiology of relevant cells thus remain unmanageable. The discovery and characterization of specific cytokines will contribute to the development of therapies for a broad range of degenerative or other conditions which affect the immune system, hematopoietic cells, as well as other cell types. The present invention provides solutions to some of these and many other problems.

SUMMARY OF THE INVENTION

The present invention is based, in part, upon biological activities of the cytokine known as IL-174. In particular, a number of assays indicate that this cytokine has functions in regulating establishment of Th2 type immune responses, innate immunity, inflammatory responses, mucosal and fibroblast growth, certain hematopoietic activities, and granuloma formation.

The present invention provides methods: directing a mammalian immune response towards a Th2 type response, the method comprising administering an IL-174 agonist to immune cells of the mammal; stimulating an mammalian innate immune response, the method comprising administering an IL-174 agonist to immune cells of the mammal; augmenting a mammalian inflammatory response from epithelial or fibroblast cells, the method comprising further administering an IL-174 agonist to the mammal; inducing gut cell growth, the method comprising administering an IL-174 agonist to the cell; promoting mammalian extra medulary hematopoiesis, the method comprising administering an IL-174 agonist to the mammal; or augmenting antibody responses in serum and fecal material, comprising administering an IL-174 agonist to the cell.

In various embodiments, the method involves administering an agonist, wherein the administering: induces cytokine production by a hematopoietic, fibroblast, epithelial, or endothelial cell; downregulates an inflammatory response which accompanies an infection; stimulates growth of an epithelial cell; or induces growth of gut epithelial, fibroblast, or goblet cells. In some embodiments, the method involves administering an agonist, wherein the mammal exhibits, or has experienced conditions to stimulate: an autoimmune condition; an infectious disease immune response; a wound healing response; or a Th1 mediated condition. In further embodiments, the autoimmune condition is selected from: multiple sclerosis, systemic lupus erythematosis, rheumatoid arthritis, diabetes, or psoriasis; the infectious response is symptomatic of: an Aspergillis infection, a fungal infection (including Candidaisis, Blastomycosis, or Aspergillosis), a parasitic infection (including Schistosomiasis, fluke worm, Helminth, or Filariasis); or a viral infection (including hepatitis); or the Th1 mediated condition is an inflammatory condition (including Crohn's disease, ulcerative colitis, pancreatitis, or hepatitis). Additionally, the invention provides methods treating an infectious response, further comprising administering another therapeutic entity to treat the infection.

The invention also provides other methods, e.g., directing a mammalian immune response away from a Th2 type response, the method comprising administering an IL-174 antagonist to immune cells of the mammal; or preventing mammalian inflammation or granuloma formation, comprising administering an IL-174 antagonist to immune system cells. Often, the antagonist is a monoclonal or polyclonal antibody against IL-174. The method may involve administering an antagonist, wherein: the administering blocks eosinophil attraction, tissue remodeling, or fibrosis; or the mammal exhibits, or has experienced conditions to stimulate: an allergic condition; an inflammatory condition; or a Th2 mediated condition. In further embodiments, the eosinophils are attracted to the lung (i.e., asthma), liver or intestine (i.e., eosinophilic gastritis); the fibrosis is pancreatic duct or peribiliary fibrosis; the antagonist suppresses production of IL-4, IL-5, and/or IL-13; the antagonist decreases eotaxin, CCR4, and/or CCR4 expression in BAL; symptoms of the allergic condition are in the lung; the allergic condition is a systemic anaphylactic response, skin hypersensitivity response, or a food allergy; or the inflammatory or Th2 mediated condition is a dermatitis or asthmatic inflammation. In yet other embodiments, the mammal exhibits, or has experienced conditions to stimulate: an allergic condition; an inflammatory condition; or a Th2 mediated condition.

The invention also provides a composition comprising: an IL-174 agonist and: an antimicrobial (including an antibiotic, antiviral, or antifungal compound) or a chemotherapy agent; or an IL-174 antagonist and: an allergy medicament, an asthma medicament, a dermatitis medicament, a fibrosis medicament, or eosinophilic gastritis medicament.

DETAILED DESCRIPTION OF THE INVENTION

Outline
I. General
II. Cytokine Agonists and Antagonists
   A. IL-174 and Variants
   B. Antibodies
   C. Other Molecules
III. Immunoassays
IV. Uses I. General The invention is based, in part, on the surprising discovery that the cytokine designated IL-174 has roles in various aspects of immune responses. The IL-174 is one of a family of genes encoding proteins which exhibit structural features characteristic of cytokines, particularly misted to the cytokine designated CTLA-8 (also referred to as IL-17). Rat, mouse, human forms and a viral homolog of CTLA-8 have been described and their sequences available from GenBank. See Rouvier, et al. (1993) *J. Immunol.* 150:5445–5456; Yao, et al. (1995) *Immunity* 3:811–821; Yao, et. al. (1995) *J. Immunol.* 155:5483–5486; and Kennedy et al. (1996) *J. Interferon and Cytokine Res.* 16:611–617. The CTLA-8 has activities implicated in arthritis, kidney graft rejection, tumorigenicity, virus-host interactions, and innate immunity; and appears to exhibit certain regulatory functions similar to IL-6. See PubMed (search for IL-17); Chabaud, et al. (1998) *J. Immunol.* 161: 409–414; Amin. et at. (1998) *Curr. Opin. Rheumatol.* 10:263–268; Van Kooten, et al. (1998) *J. Am. Soc. Nephrol.* 9:1526–1534: Fosslez, et al. (1998) *Int. Rev. Immunol.* 16:541–551; Knappe, et al. (1998) *J. Virol.* 72:5797–5801; Seow (1998) *Vet. Immuno. Immunopathol.* 63:139–148; and Teunissen, et al. (1998) *J. Invest. Dermatol.* 111:645–649. A report on the signaling through the NFκB transcription factor implicates a signal pathway which is used in innate immunity. Shalom-Barak, et al. (1998) *J. Biol. Chem.* 273:27467–27473.

The IL-174 cDNA sequences exhibit various features which are characteristic of mRNAs encoding cytokines, growth factors, and oncogenes. The IL-17 is the first member of this newly recognized family of cytokines related to TGF-β, and a number of members of this family designated "IL-170" have been identified. The fold for this family is predicted to be that of the TGF-β family of cytokines. The TGF-β family of cytokines, and the IL-170 family share the common feature of a cystine knot motif, characterized by a particular spacing of cysteine residues. See, e.g., Sun and Davies (1995) *Ann. Rev. Biophys. Biomolec. Struct.* 24:269–291; McDonald, et al. (1993) *Cell* 73:421–424; and Isaacs (1995) *Curr. Op. Struct. Biol.* 5:391–395. In particular, the structures suggest a number of conserved cysteines. The disulfide linkages should be cysteines 2 with 5; and 3 with 6; and 1 with 4. Functional significance of the fold similarity suggests formation of dimers for the IL-170 family. As a consequence, IL-170 dimers would bring together two cell surface receptors, through which signal transduction will occur.

These new proteins are designated CTLA-8 related, or generally IL-170, proteins. The natural proteins should be capable of mediating various physiological responses which would lead to biological or physiological responses in target cells, e.g., those responses characteristic of cytokine signaling.

Purified CTLA-8, when cultured with synoviocytes, is able to induce the secretion of IL-6 from these cells. This induction is reversed upon the addition of a neutralizing antibody raised against human CTLA-8. Endothelial, epithelial, fibroblast and carcinoma cells also exhibit responses to treatment with CTLA-8. This data suggests that CTLA-8 may be implicated in inflammatory fibrosis, e.g., psoriasis, sclerodermia, lung fibrosis, or cirrhosis. CTLA-8 may also cause proliferation of carcinomas or other cancer cells inasmuch as IL-6 often acts as a growth factor for such cells. As such, the newly discovered other related family members are likely to have similar or related biological activities.

The cytokine IL-174, from mouse and human, has been described earlier in PCT/US00/00006, which is incorporated herein by reference for all purposes. The nucleic acid sequence and the corresponding amino acid sequence encoding human IL-174 are set forth as SEQ ID Nos. 1 and 2 respectively. Important predicted structural motifs include, e.g., cAMP PK sites at 21–24, 53–56, and 95–98; Ca phosphorylation sites at 15–17, 16–18, and 45–47; myristoly sites at 12–16, 115–119, and 118–122; N-glycosyl site at 104–107; phosphorylation sites at 21, 23, 43, 53, 56, 95, 98, and 131; PKC phosphorylation sites at 41–43 and 119–121; and tyrosine kinase site at 95–102. The mouse nucleic acid and corresponding amino acid sequence encoding IL-174 are set forth as SEQ ID Nos. 3 and 4 respectively. Important predicted motifs include, e.g., cAMP PK sites at 29–32 and 61–64; Ca phosphorylation sites at 18–20, 53–55, and 67–69; myristoly site at 123–127; N-glycosylation site at 112–114; and phosphorylation sites at 29, 31, 51, 53, 61, 64, 139, and 141; and PKC phosphorylation sites at 2–4, 49–51, and 127–129.

II. Cytokine Agonists and Antagonists

Mammalian IL-174 cytokines were described previously in PCT/US00/00006. Various agonists and antagonists of the natural ligands can be produced.

A. IL-174 and Variants

IL-174 agonists will exhibit some or all of the signaling functions of the cytokine. Various mammalian IL-174 sequences may be evaluated to determine what residues are conserved across species, suggesting what residues may be changed without dramatic effects on biological activity. Alternatively, conservative substitutions are likely to retain biological activity, thus leading to variant forms of the cytokine which will retain agonist activity. Standard methods for screening mutant or variant IL-174 polypeptides will determine what sequences will be useful therapeutic agonists.

In addition, certain nucleic acid expression methods may be applied. Various promoters may be operably linked to the gene, thereby allowing for regulated expression.

Alternatively, antagonist activity may be tested for. Tests for ability to antagonize cytokine activity can be developed using assays as described below. Various ligand homologs can be created which retain receptor binding capacity, but lacking signaling capability can be prepared. Small molecules may also be screened for ability to antagonize IL-174 function. See generally Gilman, et al. (eds. 1990) *Goodman and Gilman's: The Pharmacological Bases of Therapeutics,* 8th Ed., Pergamon Press; *Remington's Pharmaceutical Sciences,* 17th ed. (1990), Mack Publishing Co., Easton, Pa., each of which is incorporated herein by reference.

B. Antibodies

The present invention provides for the use of an antibody or binding composition which specifically binds to IL-174, preferably mammalian, e.g., primate, human, cat, dog, rat, or mouse, and neutralizes the ability of the cytokine to mediate its signal. Antibodies can be raised to various IL-174 proteins, including individual, polymorphic, allelic, strain, or species variants, and fragments thereof, both in their naturally occurring (full-length) forms or in their recombinant forms. Additionally, antibodies can be raised to IL-174 polypeptides in both their native (or active) forms or in their inactive, e.g., denatured, forms, which may neutralize ligand capacity to mediate its signal. Antibodies may block the interaction of the ligand with its receptor.

A number of immunogens may be selected to produce antibodies specifically reactive, or selective for binding, with IL-174 proteins. Recombinant protein is a preferred immunogen for the production of monoclonal or polyclonal antibodies. Naturally occurring protein, from appropriate sources, e.g., primate, rodent, etc., may also be used either in pure or impure form. Synthetic peptides, made using the IL-174 protein sequences described herein, may also be used as an immunogen for the production of antibodies to IL-174 proteins. Recombinant protein can be expressed and purified in eukaryotic or prokaryotic cells as described, e.g., in Coligan, et al. (eds. 1995 and periodic supplements) *Current Protocols in Protein Science* John Wiley & Sons, New York, N.Y.; and Ausubel, et al (eds. 1987 and periodic supplements) *Current Protocols in Molecular Biology,* Greene/Wiley, New York, N.Y. Naturally folded or denatured material can be used, as appropriate, for producing antibodies. Either monoclonal or polyclonal antibodies may be generated, e.g., for subsequent use in immunoassays to measure the protein, or for immunopurification methods.

Methods of producing polyclonal antibodies are well known to those of skill in the art. Typically, an immunogen, preferably a purified protein, is mixed with an adjuvant and animals are immunized with the mixture. The animal's immune response to the immunogen preparation is monitored by taking test bleeds and determining the titer of reactivity to the IL-174 protein or peptide of interest. For example, when appropriately high titers of antibody to the immunogen are obtained, usually after repeated immunizations, blood is collected from the animal and antisera are prepared. Further fractionation of the antisera to enrich for antibodies reactive to the protein can be performed, if desired. See, e.g., Harlow and Lane *Antibodies, A Laboratory Manual* CSH Press, NY; or Coligan (ed.) *Current Protocols in Immunology.* Immunization can also be performed through other methods, e.g., DNA vector immunization. See, e.g., Wang, et al. (1997) *Virology* 228:278–284.

Monoclonal antibodies may be obtained by various techniques familiar to those skilled in the art. Typically, following immunizations, spleen cells from the animal are immortalized, commonly by fusion with a myeloma cell. See, Kohler and Milstein (1976) *Eur. J. Immunol.* 6:511–519. Alternative methods of immortalization include transformation with Epstein Barr Virus, oncogenes, or retroviruses, or other methods known in the art. See, e.g., Doyle, et al. (eds. 1994 and periodic supplements) *Cell and Tissue Culture: Laboratory Procedures,* Wiley, NY, N.Y.

Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) *Science* 246:1275–1281.

Antibodies or binding compositions, including binding fragments and single chain versions, against predetermined fragments of IL-174 polypeptides can be raised by immunization of animals with conjugates of the fragments with carrier proteins as described above. Monoclonal antibodies are prepared from cells secreting the desired antibody.

These antibodies can be screened for binding to normal or defective IL-174 protein. These monoclonal antibodies will usually bind with at least a $K_D$ of about 1 mM, more usually at least about 300 $\mu$M, typically at least about 10 $\mu$M, more typically at least about 30 $\mu$M, preferably at least about 10 $\mu$M, and more preferably at least about 3 $\mu$M or better.

In some instances, it is desirable to prepare monoclonal antibodies (mAbs) from various mammalian hosts, such as mice, rodents, primates, humans, etc. Description of techniques for preparing such monoclonal antibodies may be found in, e.g., Stites, et al. (eds.) *Basic and Clinical Immunology* (4th ed.) Lange Medical Publications, Los Altos, Calif., and references cited therein; Harlow and Lane (1988) *Antibodies: A Laboratory Manual* CSH Press; Goding (1986) *Monoclonal Antibodies: Principles and Practice* (2d ed.) Academic Press, New York, N.Y.; and particularly in Kohler and Milstein (1975) *Nature* 256:495–497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, e.g., Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see, Cabilly, U.S. Pat. No. 4,816,567; and Queen, et al. (1989) *Proc. Nat'l Acad. Sci. USA* 86:10029–10033; or made in transgenic mice, see Mendez, et al. (1997) *Nature Genetics* 15:146–156; Abgenix and Medarex technologies.

Antibody binding compounds, including binding fragments, of this invention can have significant diagnostic or therapeutic value. They can be useful as non-neutralizing binding compounds and can be coupled to toxins or radionuclides so that when the binding compound binds to the antigen, a cell expressing it, e.g., on its surface, is killed. Further, these binding compounds can be conjugated to drugs or other therapeutic agents, either directly or indirectly by means of a linker, and may effect drug targeting.

C. Other Molecules

Antibodies are merely one form of specific binding compositions. Other binding compositions, which will often have similar uses, include molecules that bind with specificity to IL-174, e.g., in a protein-binding partner fashion, an antibody-antigen interaction, or in a natural physiologically relevant protein—protein interaction, either covalent or non-covalent, e.g., proteins which specifically associate with IL-174 protein. The molecule may be a polymer, or chemical reagent. A functional analog may be a protein with structural modifications, or may be a structurally unrelated molecule, e.g., which has a molecular shape which interacts with the appropriate binding determinants.

Drug screening using antibodies or IL-174 or fragments thereof can be performed to identify compounds having binding affinity to IL-174, or can block or simulate the natural interaction with ligand. Subsequent biological assays can then be utilized to determine if the compound has intrinsic blocking activity and is therefore an antagonist. Likewise, a compound having intrinsic stimulating activity can signal to the cells via the IL-174 pathway and is thus an agonist in that it simulates the activity of a ligand. Mutein antagonists may be developed which maintain receptor binding but lack signaling.

Structural studies of the ligands will lead to design of new variants, particularly analogs exhibiting agonist or antagonist properties on the receptor. This can be combined with previously described screening methods to isolate muteins exhibiting desired spectra of activities.

As receptor specific binding molecules are provided, also included are small molecules identified by screening procedures. In particular, it is well known in the art how to screen for small molecules which interfere, e.g., with ligand binding to the receptor, often by specific binding to the receptor and blocking of binding by natural ligand. See, e.g., meetings on High Throughput Screening, International Business Communications, Southborough, Mass. 01772-1749. Such molecules may compete with natural ligands, and selectively bind to the IL-174.

III. Immunoassays

Immunoassays are valuable in diagnosing a disease or disorder associated with IL-174 imbalance or pathology. Qualitative or quantitative measurement of a particular protein can be performed by a variety of immunoassay methods. For a review of immunological and immunoassay procedures in general, see Stites and Terr (eds.) (1991) *Basic and Clinical Immunology* (7th ed.). Moreover, the immunoassays of the present invention can be performed in many configurations, which are reviewed extensively in Maggio (ed. 1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B. V., Amsterdam; and Harlow and Lane *Antibodies: A Laboratory Manual*, supra. See also Chan (ed. 1987) *Immunoassay: A Practical Guide* Academic Press, Orlando, Fla.; Price and Newman (eds. 1991) *Principles and Practice of Immunoassays* Stockton Press, NY; and Ngo (ed. 1988) *Non-isotopic Immunoassays* Plenum Press, NY.

Immunoassays for measurement of IL-174 proteins or peptides can be performed by a variety of methods known to those skilled in the art. In brief, immunoassays to measure the protein can be either competitive or noncompetitive binding assays. In competitive binding assays, the sample to be analyzed competes with a labeled analyte for specific binding sites on a capture agent bound to a solid surface. Preferably the capture agent is an antibody specifically reactive with IL-174 proteins produced as described above. The concentration of labeled analyte bound to the capture agent is inversely proportional to the amount of free analyte present in the sample.

In a competitive binding immunoassay, the IL-174 protein present in the sample competes with labeled protein for binding to a specific binding agent, e.g., an antibody specifically reactive with IL-174 protein. The binding agent may be bound to a solid surface to effect separation of bound labeled protein from the unbound labeled protein. Alternatively, the competitive binding assay may be conducted in liquid phase and a variety of techniques known in the art may be used to separate the bound labeled protein from the unbound labeled protein. Following separation, the amount of bound labeled protein is determined. The amount of protein present in the sample is inversely proportional to the amount of labeled protein binding.

Alternatively, a homogeneous immunoassay may be performed in which a separation step is not needed. In these immunoassays, the label on the protein is altered by the binding of the protein to its specific binding agent. This alteration in the labeled protein results in a decrease or increase in the signal emitted by label, so that measurement of the label at the end of the immunoassay allows for detection or quantitation of the protein.

IL-174 proteins may also be determined by a variety of noncompetitive immunoassay methods. For example, a two-site, solid phase sandwich immunoassay may be used. In this type of assay, a binding agent for the protein, for example an antibody, is attached to a solid support. A second protein binding agent, which may also be an antibody, and which binds the protein at a different site, is labeled. After binding at both sites on the protein has occurred, the unbound labeled binding agent is removed and the amount of labeled binding agent bound to the solid phase is measured. The amount of labeled binding agent bound is directly proportional to the amount of protein in the sample.

Western blot analysis can be used to determine the presence of IL-174 proteins in a sample. Electrophoresis is carried out, e.g., on a tissue sample suspected of containing the protein. Following electrophoresis to separate the proteins, and transfer of the proteins to a suitable solid support, e.g., a nitrocellulose filter, the solid support is incubated with an antibody reactive with the protein. This antibody may be labeled, or alternatively may be detected by subsequent incubation with a second labeled antibody that binds the primary antibody.

The immunoassay formats described above may employ labeled assay components. The label may be coupled directly or indirectly to the desired component of the assay according to methods well known in the art. A wide variety of labels and methods may be used. Traditionally, a radioactive label incorporating $^3$H, $^{125}$I, $^{35}$S, $^{14}$C, or $^{32}$P was used. Non-radioactive labels include ligands which bind to labeled antibodies, fluorophores, chemiluminescent agents, enzymes, and antibodies which can serve as specific binding pair members for a labeled ligand. The choice of label depends on sensitivity required, ease of conjugation with the compound, stability requirements, and available instrumentation. For a review of various labeling or signal producing systems which may be used, see U.S. Pat. No. 4,391,904.

Antibodies reactive with a particular protein can also be measured by a variety of immunoassay methods. Thus modifications of the above procedures may be used to determine the amounts or affinities of various IL-174 antibodies or antibody preparations. For a review of immunological and immunoassay procedures applicable to the measurement of antibodies by immunoassay techniques, see Stites and Terr (eds.) *Basic and Clinical Immunology* (7th ed.) supra; Maggio (ed.) *Enzyme Immunoassay,* supra; and Harlow and Lane *Antibodies, A Laboratory Manual,* supra.

Screens to evaluate the binding and activity of mAbs and binding compositions encompass a variety of methods. Binding can be assayed by detectably labeling the antibody or binding composition as described above. Cells responsive to IL-174 can be used to assay antibody or binding composition.

Evaluation of antibodies can be performed in other animals, e.g., humans using various methods. For example, blood samples are withdrawn from patients suffering from an indicated disease or disorder before and after treatment, e.g., with a candidate mAb.

IV. Uses

IL-174 now has demonstrated effects on various cells, which effects may be indirect, as well as direct. A statistically significant change in the numbers or effects on cells will typically be at least about 10%, preferably 20%, 30%, 50%, 70%, 90%, or more. Effects of greater than 100%, e.g., 130%, 150%, 2x, 3x, 5x, etc., will often be desired. The effects may be specific in reducing symptoms or signs of the indicated conditions.

The present invention is useful in the treatment of medical conditions or diseases associated with immunological conditions described. See, e.g., Frank, et al. (eds. 1995) *Samter's Immunologic Diseases,* 5th Ed., vols. I–II, Little, Brown and Co., Boston, Mass. The agonists or antagonists described may be combined with other treatments of the medical conditions described herein, e.g., another cytokine involved in Th1/Th2 balance (such as IL-1γ and/or IL-12 to Th1; or IL-4 to Th2), an antibiotic, immune suppressive therapeutic, immune adjuvant, analgesic, anti-inflammatory drug, growth factor, vasodilator, or vasoconstrictor.

Preferred combination therapies include IL-174 agonists with various therapeutics which promote Th2 type immune responses (e.g., IL-4, IL-1γ antagonists, IL-12 antagonists), inflammatory agents, such as topical, transdermal, or systemic irritants, various growth factors, and hematopoietic factors. Antagonists of IL-174, e.g., antibodies or ligand muteins, can be combined with therapeutics which promote Th1 type immune responses (e.g., IL-1γ and/or IL-12, IL-4 antagonists), or anti-inflammatories (e.g., steroids, glucocortical steroids).

Standard immunological techniques are described, e.g., in Hertzenberg, et al. (eds. 1996) *Weir's Handbook of Experimental Immunology* vols. 1–4, Blackwell Science; Coligan (1991) *Current Protocols in Immunology* Wiley/Greene, NY; and *Methods in Enzymology* volumes 70, 73, 74, 84, 92, 93, 108, 116, 121, 132, 150, 162, and 163. These will allow use of the reagents for purifying cell subpopulations, etc.

To prepare pharmaceutical or sterile compositions including IL-174, antagonists, or combinations, the reagent is admixed with a pharmaceutically acceptable carrier or excipient which is preferably inert. Preparation of such pharmaceutical compositions is known in the art, see, e.g., *Remington's Pharmaceutical Sciences* and *U.S. Pharmacopeia: National Formulary,* Mack Publishing Company, Easton, Pa. (1984).

Agonists, e.g., natural ligand, or antagonists, e.g., antibodies or binding compositions, are normally administered parenterally, preferably intravenously. Since such protein or peptide antagonists may be immunogenic they are preferably administered slowly, either by a conventional IV administration set or from a subcutaneous depot, e.g. as taught by Tomasi, et al., U.S. Pat. No. 4,732,863.

When administered parenterally the therapeutics will often be formulated in a unit dosage injectable form (solution, suspension, emulsion) in association with a pharmaceutically acceptable parenteral vehicle. Such vehicles are typically inherently nontoxic and nontherapeutic. Agonists, which typically will be smaller biologics, will typically be administered in smaller doses than antibody biologics. The antagonist may be administered in aqueous vehicles such as water, saline or buffered vehicles with or without various additives and/or diluting agents. Alternatively, a suspension, such as a zinc suspension, can be prepared to include the peptide. Such a suspension can be useful for subcutaneous (SQ), intradermal (ID), or intramuscular (IM) injection. The proportion of therapeutic entity and additive can be varied over a broad range so long as both are present in effective amounts. The therapeutic is preferably formulated in purified form substantially free of aggregates, other proteins, endotoxins, and the like, at concentrations of about 5 to 30 mg/ml, preferably 10 to 20 mg/ml. Preferably, the endotoxin levels are less than 2.5 EU/ml. See, e.g., Avis, et al. (eds. 1993) *Pharmaceutical Dosage Forms: Parenteral Medications* 2d ed., Dekker, N.Y.; Lieberman, et al. (eds. 1990) *Pharmaceutical Dosage Forms: Tablets* 2d ed., Dekker, N.Y.; Lieberman, et al. (eds. 1990) *Pharmaceutical Dosage Forms: Disperse Systems* Dekker, N.Y.; Fodor, et al. (1991) *Science* 251:767–773; Coligan (ed.) *Current Protocols in Immunology;* Hood, et al. *Immunology* Benjamin/Cummings; Paul (ed. 1997) *Fundamental Immunology* 4th ed., Academic Press; Parce, et al. (1989) *Science* 246:243–247; Owicki, et al. (1990) *Proc. Nat'l Acad. Sci. USA* 87:4007–4011; and Blundell and Johnson (1976) *Protein Crystallography,* Academic Press, New York.

Selecting an administration regimen for a therapeutic agonist or antagonist depends on several factors, including the serum or tissue turnover rate of the therapeutic, the immunogenicity of the therapeutic, or the accessibility of the target cells. Preferably, an administration regimen maximizes the amount of therapeutic delivered to the patient consistent with an acceptable level of side effects. Accordingly, the amount of therapeutic delivered depends in part on the particular agonist or antagonist and the severity of the condition being treated. Guidance in selecting appropriate doses of antibodies is found in the literature on therapeutic uses, e.g. Bach et al., chapter 22, in Ferrone, et al. (eds. 1985), *Handbook of Monoclonal Antibodies* Noges Publications, Park Ridge, N.J.; and Russell, pgs. 303–357, and Smith et al., pgs. 365–389, in Haber, et al. (eds. 1977) *Antibodies in Human Diagosis and Therapy* Raven Press, New York, N.Y.

Determination of the appropriate dose is made by the clinician, e.g., using parameters or factors known in the art to affect treatment or predicted to affect treatment. Generally, the dose begins with an amount somewhat less than the optimum dose and it is increased by small increments thereafter until the desired or optimum effect is achieved relative to any negative side effects. Preferably, an antibody or binding composition thereof that will be used is derived from the same species as the animal targeted for treatment, thereby minimizing a humoral response to the reagent.

The total weekly dose ranges for antibodies or fragments thereof, which specifically bind to IL-174, range generally from about 1 ng, more generally from about 10 ng, typically from about 100 ng; more typically from about 1 µg, more typically from about 10 µg, preferably from about 100 µg, and more preferably from about 1 mg per kilogram body weight. Although higher amounts may be more efficacious, the lower doses typically will have fewer adverse effects. Generally the range will be less than 100 mg, preferably less than about 50 mg, and more preferably less than about 25 mg per kilogram body weight.

The weekly dose ranges for antagonists, e.g., antibody, binding fragments, range from about 10 µg, preferably at least about 50 µg, and more preferably at least about 100 µg. per kilogram of body weight. Generally, the range will be less than about 1000 µg, preferably less than about 500 µg, and more preferably less than about 100 µg per kilogram of body weight. Dosages are on a schedule which effects the desired treatment and can be periodic over shorter or longer term. In general, ranges will be from at least about 10 µg to about 50 mg, preferably about 100 µg to about 10 mg per kilogram body weight.

Agonists, or other antagonists of the ligands, e.g., muteins, are also contemplated. Hourly dose ranges for cytokine or muteins range from at least about 10 µg, generally at least about 50 µg, typically at least about 100 µg, and preferably at least 500 µg per hour. Generally the dosage will be less than about 100 mg, typically less than about 30 mg, preferably less than about 10 mg, and more preferably less than about 6 mg per hour. General ranges will be from at least about 1 µg to about 1000 µg, preferably about 10 µg to about 500 µg per hour.

The present invention also provides for administration of IL-174 antibodies or binding compositions in combination with known therapies, e.g., therapeutics which alleviate the symptoms associated with excessive inflammatory responses, such as steroids, particularly glucocorticoids. Daily dosages for glucocorticoids will range from at least about 1 mg, generally at least about 2 mg, and preferably at least about 5 mg per day. Generally, the dosage will be less than about 100 mg, typically less than about 50 mg, preferably less than about 20 mg, and more preferably at least about 10 mg per day. In general, the ranges will be from at least about 1 mg to about 100 mg, preferably from about 2 mg to 50 mg per day.

The phrase "effective amount" means an amount sufficient to effect a desired response, or to ameliorate a symptom or sign of the indicated condition. Typical mammalian hosts will include mice, rats, cats, dogs, and primates, including humans. An effective amount for a particular patient may vary depending on factors such as the condition being treated, the overall health of the patient, the method, route, and dose of administration and the severity of side affects. Preferably, the effect will result in a change in quantitation of at least about 10%, preferably at least 20%, 30%, 50%, 70%, or even 90% or more. When in combination, an effective amount is in ratio to a combination of components and the effect is not limited to individual components alone.

An effective amount of therapeutic will modulate the symptoms typically by at least about 10%; usually by at least about 20%; preferably at least about 30%; or more preferably at least about 50%. Alternatively, modulation of movement will mean that the movement or trafficking of various cell types is affected. Such will result in, e.g., statistically significant and quantifiable changes in the numbers of cells being affected. This may be an increase or decrease in the numbers of target cells being attracted within a time period or target area.

The present invention provides reagents which will find use in therapeutic applications as described elsewhere herein, e.g., in the general description for treating disorders associated with the indicated conditions. See, e.g., Berkow (ed.) *The Merck Manual of Diagnosis and Therapy*, Merck & Co., Rahway, N.J.; Thorn, et al. *Harrison's Principles of Internal Medicine*, McGraw-Hill, N.Y.; Gilman, et al. (eds. 1990) *Goodman and Gilman's: The Pharmacological Bases of Therapeutics*, 8th Ed., Pergamon Press; *Remington's Pharmaceutical Sciences*, 17th ed. (1990), Mack Publishing Co., Easton, Pa.; Langer (1990) *Science* 249:1527–1533; and *Merck Index*, Merck & Co., Rahway, N.J.

Antibodies to IL-174 proteins may be used for the identification or sorting of cell populations expressing IL-174 protein. Methods to sort such populations are well known in the art, see, e.g., Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y. Populations of cells expressing the IL-174 receptor can also be purified using magnetic beads as described, e.g., in Bieva, et al. (1989) *Exp. Hematol.* 17:914–920; Hernebtub, et al. (1990) *Bioconj. Chem.* 1:411–418; Vaccaro (1990) *Am. Biotechnol. Lab.* 3:30.

Moreover, antisense nucleic acids may be used. For example, antisense constructs specific to nucleic acids encoding, e.g., the ligand, may function in a manner like ligand antagonists, and antisense constructs specific to those encoding the receptor may function like receptor antagonists. See, e.g., Stepkowski, et al. (1998) *Transplantation* 66:699–707; and ISIS Pharmaceuticals technology. Thus, it may be possible to block the signaling through these pathways with antisense nucleic acids.

Using the assay methods described above, the antibodies or binding compositions are useful in diagnosing disease states which result in the indicated disorders. Antibodies raised against an IL-174 protein will also be useful to raise anti-idiotypic antibodies. These will be useful in detecting or diagnosing various immunological conditions related to expression of the respective antigens. Combinations of these signals may be also pursued.

The broad scope of this invention is best understood with reference to the following examples, which are not intended to limit the inventions to the specific embodiments.

EXAMPLES

I. General Methods

The cytokine IL-174, from mouse and human, has been described earlier in PCT/US00/00006, which is incorporated herein by reference for all purposes.

Some of the standard methods are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols. 1–3, CSH Press, NY; Ausubel, et al., *Biology*, Greene Publishing Associates, Brooklyn, N.Y.; or Ausubel, et al. (1987 and Supplements) *Current Protocols in Molecular Biology*, Greene/Wiley, New York; Innis, et al. (eds.)(1990) *PCR Protocols: A Guide to Methods and Applications* Academic Press, N.Y. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology*, vol. 182, and other volumes in this series; manufacturer's literature on use of protein purification products, e.g., Pharmacia, Piscataway, N.J., or Bio-Rad, Richmond, Calif.; and Coligan, et al. (eds.) (1995 and periodic supplements) *Current Protocols in Protein Science,* John Wiley & Sons, New York, N.Y. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *QIAexpress: The High Level Expression & Protein Purification System* QIAGEN, Inc., Chatsworth, Calif.

Standard immunological techniques are described, e.g., in Hertzenberg, et al. (eds. 1996) *Weir's Handbook of Experimental Immunology* vols. 1–4, Blackwell Science; Coligan (1991) *Current Protocols in Immunology* Wiley/Greene, NY; and *Methods in Enzymology* vols. 70, 73, 74, 84, 92, 93, 108, 116, 121, 132, 150, 162, and 163.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Antibody Production

Appropriate mammals are immunized with appropriate amounts of IL-174 gene transfected cells, e.g., intraperitoneally every 2 weeks for 8 weeks. Typically, rodents are used, though other species should accommodate production of selective and specific antibodies. The final immunization is given intravenously (IV) through the tail vein.

Generic polyclonal antibodies may be collected. Alternatively, monoclonal antibodies can be produced. For example, four days after the IV injection, the spleen is removed and fused to SP2/0 and NS1 cells. HAT resistant hybridomas are selected, e.g., using a protocol designed by Stem Cell Technologies (Vancouver, BC). After 10 days of HAT selection, resistant foci are transferred to 96 well plates and expanded for 3 days. Antibody containing supernatants are analyzed, e.g., by FACS for binding to NIH3T3/surface IL-174 transfectants. Many different IL-174 mAbs are typically produced. Those antibodies may be isolated and modified, e.g., by labeling or other means as is standard in the art. See, e.g., Harlow and Lane (1988) *Antibodies: A Laboratory Manual* CSH Press; Goding (1986) *Monoclonal Antibodies: Principles and Practice* (2d ed.) Academic Press, New York, N.Y. Methods to conjugate magnetic reagents, toxic entities, labels, attach the antibodies to solid substrates, to sterile filter, etc., are known in the art.

III. IL-174 Antagonists

Various antagonists of IL-174 are made available. For example, antibodies against the cytokine itself may block the binding of ligand to its receptor, thereby serving as a direct receptor antagonist. Other antagonists may function by blocking the binding of ligand to receptor, e.g., by binding to the ligand in a way to preclude the possibility of binding to the receptor. Other antagonists, e.g., mutein antagonists, may bind to the receptor without signaling, thereby blocking a true agonist from binding. Many of these may serve to block the signal transmitted to target cells, specifically IL-174 responsive cells.

Information on the criticality of particular residues is determined using standard procedures and analysis. Standard mutagenesis analysis is performed, e.g., by generating many different variants at determined positions, e.g., at the positions identified above, and evaluating biological activities of the variants. This may be performed to the extent of determining positions which modify activity, or to focus on specific positions to determine the residues which can be substituted to either retain, block, or modulate biological activity.

Alternatively, analysis of natural variants can indicate what positions tolerate natural mutations. This may result from populational analysis of variation among individuals, or across strains or species. Samples from selected individuals are analyzed, e.g., by PCR analysis and sequencing. This allows evaluation of population polymorphisms.

IV. Adenoviral Infection

Adenovirus constructs were prepared. Mice were infected with adenovirus-IL-74 via the intranasal route or the intravenous route. See, e.g., Hitt, et al. (1997) *Adv. Pharmacol.* 40:137–195. The doses of adenovirus-IL-74 given ranged from $5 \times 10^9$ to $5 \times 10^{10}$ particles. Mice were evaluated 7, 14, 21, and 35 days post infection using standard histologic, immunologic, and hematologic methods V. Histologic Analysis Tissues from mice were fixed in formalin, routinely processed, sectioned, and stained with hematoxylin and eosin for microscopic examination. The organs examined included the lung, heart, liver, kidney, spleen, bone marrow, and gastrointestinal tract. See, e.g., Kerr (1999) *Atlas of Functional Histology;* Sternberg (ed. 1998) *Histology for Pathologists;* and Stevens and Lowe (1996) *Human Histology.*

VI. Hematopoietic Colony Forming Assays

Hematopoietic progenitors in the spleens of mice were enumerated in routine colony-forming assays. Spleen cells were depleted of erythrocytes by hypotonic lysis. Spleen cells were incubated with unmodified rat monoclonal antibodies specific for CD2 (RM2.2; see Yagata, et al. (1989) *Proc. Nat'l Acad. Sci. USA* 86:645–649), CD8 (53.6.7; see Ledbetter, et al. *Immunol. Rev.* 47:63–90), B220 (RA3–6B2; see Coffman, et al. (1981) *Nature* 289:681–683), Mac1 (M1/70; see Springer, et al. (1979) *Eur. J. Immunol.* 9:301–306), GR1 (RB6–8C5; see Julia, et al. (1988) *Eur. J. Immunol.* 19:1819–1826), and erythrocytes (Ter-119; see Spangrude, et al. (1990) *Exp. Hemat.* 18:920–926). The lineage positive cells depleted by negative selection using goat anti-rat coated BioMagR beads (PerSeptive Biosystems, Framingham, Mass.) in two successive rounds of treatment. The remaining lineage negative spleen cells were seeded in 35 mm culture dishes containing 1 ml modified Iscove's medium (JRH, Kansas City, Kans.), 20% fetal calf serum (FCS) (JRH) 50 mM 2-mercaptoethanol, and 0.8% (wt/vol) methylcellulose. All cultures were supplemented with saturating concentrations of various growth factors. Cultures were incubated at 37° C. in a humidified atmosphere flushed with 5% CO2. After 10 days of incubation, colonies were analyzed for number and size. Cell morphologies were determined after colonies were applied to glass slides and stained with Wright's Giemsa for microscopic examination. See Metcalf (1984) *The Hemopoietic Colony Stimulating Factors,* Elsevier, Amsterdam.

VII. Blood Cell Analysis

Blood from mice was collected in Isotonic Buffered Diluent (BioChem ImmunoSystems, Allentown, Pa.) and hemoglobin, hematocrit, white blood cell, red blood cell, and platelet counts were determined by an automatic cell counter (Serono 9010, Serono-Baker Diagnostics, Inc., Allentown, Pa.). Blood smears were stained with Wright's Giemsa and differential counts were performed with the aid of a microscope. See, e.g., Dainiak (1990) *The Biology of Hematopoiesis,* Wiley-Liss Inc., New York; Testa and Molineux (1993) *Haemopoiesis,* Oxford University Press, New York.

VIII. Determination of Antibody Isotypes

Sera from mice were serially diluted in isotonic buffer in microtiter wells coated with rat anti-mouse heavy-chain class-specific antibodies (anti-α, -γ1, -γ2a, and -ε). A biotinylated secondary antibody (specific for heavy-chain classes) was added and then reacted with streptavidin-HRP (Jackson ImmunoResearch Laboratories Inc., West Grove, Pa.). The colored product produced by this TMB peroxidase substrate system (Kirkegaard & Perry Laboratories, Gaithersburg, Md.) is detected under a long-wavelength UV lamp (450 nanometers). See, e.g., Coligan, et al. (eds. 1991 and supplements) *Current Protocols in Immunology*, Greene/Wiley.

IX. Bronchio-Alveolar Lavage Fluid Analysis

Bronchio-alveolar lavage (BAL) fluid was collected from sacrificed mice by inserting a needle into the trachea and dispensing 1 ml of DMEM media. 200 μl of the recovered sample was examined for cell composition by cytospin followed by Wright-Giemsa stain. Differential counts were performed with the aid of a microscope.

X. Quantification of Gene Expression by Real-Time RT-PCR

Sample tissues were excised from mice following treatment and were snap-frozen in liquid nitrogen. Total RNA was extracted using RNAstat60 (Molecular Research Center) according to the manufacturer's directions and were stored at −80° C. in nuclease-free. For cDNA synthesis RNA was incubated with 10 units of DNase I (Boehringer Mannheim) in the presence of RNasin (Promega) for 30 minutes at 37° C. The samples were then heat inactivated at 95° C. for 10 minutes, chilled, and reverse transcribed with Superscript II reverse transcriptase (Gibco/BRL) with random hexamers according to the manufacturer's protocol. Primers were either obtained from Perkin Elmer or generated with Primer Express software (Perkin Elmer) and were synthesized in the DNAX primer core facility. Whenever possible, primer pairs were designed to span intron/exon borders. Samples were then subjected to 40 cycles of amplification of 95° C. for 15 seconds followed by 60° C. for 1 minute using an ABI GeneAmp 5700 sequence detection system and SYBR green buffer according to the manufacturer (Perkin Elmer). PCR amplification of the housekeeping gene ubiquitin was performed for each sample to control for sample loading and to allow normalization between samples according to the manufacturer's instructions (Perkin Elmer). Both water and genomic DNA controls were included to insure specificity. Each data point was examined for integrity by analysis of the amplification plot and disassociation curves.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the fall scope of equivalents to which such claims are entitled; and the invention is not to be limited by the specific embodiments that have been presented herein by way of example.

What is claimed is:

1. A method of treating a mammal exhibiting an allergic condition comprising administering an effective amount of an IL-174 antagonist sufficient to ameliorate the allergic condition.

2. The method of claim 1, wherein the IL-174 antagonist inhibits production of IL-4, IL-5, IL-13, eotaxin, or CCR4.

3. The method of claim 1, wherein the IL-174 antagonist inhibits:

a) eosinophil attraction to the lung; or
   b) fibrosis.

4. The method of claim 1, wherein the allergic condition is:

a) a respiratory condition;
   b) a systemic anaphylactic response;
   c) a skin hypersensitivity response; or
   d) a food allergy.

5. The method of claim 1, wherein the IL-174 antagonist comprises:

a) a polyclonal antibody;
   b) a monoclonal antibody;
   c) an antibody fragment; or
   d) a humanized antibody.

* * * * *